United States Patent [19]

Miyake

[11] Patent Number: 5,561,482
[45] Date of Patent: Oct. 1, 1996

[54] EYE REFRACTIVE POWER MEASURING APPARATUS WITH ORIENTATION DEPENDENT DISCRIMINATION BETWEEN RIGHT AND LEFT EYES

[75] Inventor: Nobuyuki Miyake, Yokohama, Japan

[73] Assignee: Nikon Corporation, Tokyo, Japan

[21] Appl. No.: 378,012

[22] Filed: Jan. 25, 1995

[30] Foreign Application Priority Data

Feb. 4, 1994 [JP] Japan .................................. 6-012697

[51] Int. Cl.⁶ .............................. A61B 3/14; A61B 3/10
[52] U.S. Cl. ......................... 351/208; 351/211; 351/221
[58] Field of Search ................................. 351/205, 200, 351/211, 212, 218, 219, 217, 216, 221, 246, 208, 210, 209

[56] References Cited

U.S. PATENT DOCUMENTS 4,353,625  10/1982  Nohda et al. ............................. 351/13

FOREIGN PATENT DOCUMENTS 62-5147  1/1987  Japan .
4-73046  3/1992  Japan .

*Primary Examiner*—Hung X. Dang
*Attorney, Agent, or Firm*—Shapiro and Shapiro

[57] ABSTRACT

An eye refractive power measuring apparatus is provided with a measuring device opposed to eyes to be examined for measuring the eye refractive power of the eyes to be examined, an eye-to-be-examined detecting device for detecting whether the eye to which the measuring device is opposed is one or the other of the eyes to be examined, a designating switch for designating the direction in which the measuring device is opposed to the eyes to be examined, and a judging whether the eye to be examined is device for judging a right eye or a left eye based on the result of the detection by the eye-to-be-examined detecting device and the direction designated by the designating switch.

11 Claims, 11 Drawing Sheets

EYE REFRACTIVE POWER MEASURING APPARATUS WITH ORIENTATION DEPENDENT DISCRIMINATION BETWEEN RIGHT AND LEFT EYES

BACKGROUND OF THE INVENTION

1. Field of the Invention

This invention relates to an eye refractive power measuring apparatus.

2. Related Background Art

As an ophthalmologic instrument for effecting the observation or measurement of an examinee's eye, for example, an eye refractive power measuring apparatus for automatically measuring the examinee's eye refractive power is known under the name of an auto refractometer, and is described in U.S. Pat. No. 4,353,625 and Japanese Patent Application Laid-Open No. 62-5147. This measuring apparatus measures the eye refractive power when the optical axis of the examinee's eye and the optical axis of the measuring apparatus coincide with each other. The direction of the astigmatism axis (cylindrical axis) of the eye to be examined is also measured as part of the eye refractive power. The direction of the astigmatism axis is represented by coordinates with the eye to be examined as the reference.

Generally, the measuring part of this measuring apparatus is placed on a sliding stand movable right and left and back and forth, with a view to measure right and left eyes. In this case, discrimination as to which of the right and left eyes is being measured has been effected by obtaining information indicating whether the measuring part is on the right or left side of the sliding stand.

Recently, demand has been strong for measuring the eye refractive power during various operations, and compact and manually holdable eye refractive power measuring apparatuses have been introduced. However, when the apparatus becomes manually holdable, it becomes impossible to discriminate between right and left eyes based on the position of the measuring part on the sliding stand, as has heretofore been done.

As a manually holdable apparatus capable of discriminating between right and left eyes, there is an eye examining apparatus described in Japanese Patent Application Laid-Open No. 4-73046. This apparatus is provided with a light source emitting a beam of light for illuminating the sideways part of an eye to be examined, and a photoelectric sensor for receiving the reflected light of said beam of light, and discriminates between right and left eyes.

This eye examining apparatus, however, can measure only from a certain predetermined direction relative to the eye to be examined. For example, when an examinee is to be measured while lying down on a bed or the like in a hospital, the measuring apparatus is unavoidably used from the bed side and necessarily, the apparatus is used in opposed relationship with the eye to be examined from various directions.

Usually, when the direction of the astigmatism axis is to be measured, the direction of the astigmatism axis is measured on coordinate system with the measuring apparatus as the reference.

Accordingly, when the measuring apparatus is used in various directions relative to the eye to be examined, the coordinate system with the eye to be examined as the reference and the coordinate system with the measuring apparatus as the reference do not coincide with each other in some cases. At such time, the actual direction of the astigmatism axis on the coordinate system with the eye to be examined as the reference and the direction of the astigmatism axis on the coordinate system with the measuring apparatus as the reference deviate from each other.

SUMMARY OF THE INVENTION

It is an object of the present invention to provide an eye refractive power measuring apparatus which can determine which of the right and left eyes is being examined even if measurement is effected in any of vertical and horizontal directions relative to the eye to be examined.

The above object is achieved by an eye refractive power measuring apparatus provided with a measuring device for measuring the eye refractive power of eyes to be examined, an eye-to-be-examined detecting device for detecting whether the eye which said measuring device is opposed to is one or the other of said eyes to be examined, a designating switch for designating the direction in which said measuring device is opposed to said eyes to be examined, and a judging device for judging whether an eye to be examined opposed to the measuring apparatus is a right eye or a left eye based on the result of the detection by said eye-to-be-examined detecting device and the direction designated by said designating switch.

It is also an object of the present invention to provide an eye refractive power measuring apparatus for correcting the direction of an astigmatism axis in conformity with each said direction.

The above object is achieved by an eye refractive power measuring apparatus in which said judging device corrects the direction of an astigmatism axis of said eyes to be examined based on said direction designating by the designating switch.

With the eye refractive power measuring apparatus, it is possible to discriminate between the right and left eyes of the eyes to be examined when measurement is effected with the measuring apparatus opposed to the eyes to be examined in any of the vertical and horizontal directions. Also, the correction of the direction of an astigmatism axis of the eyes to be examined can be effected together on the basis of the result of an input to said direction designating means.

BRIEF DESCRIPTION OF THE DRAWINGS

2FIG. 6 is an illustration showing a state in which the eye refractive power measuring apparatus of FIG. 1 is effecting left eye measurement in the downward direction relative to the eye to be examined.

DESCRIPTION OF THE PREFERRED EMBODIMENTS

Embodiments of the present invention will hereinafter be described with reference to the drawings.

Figure 1:
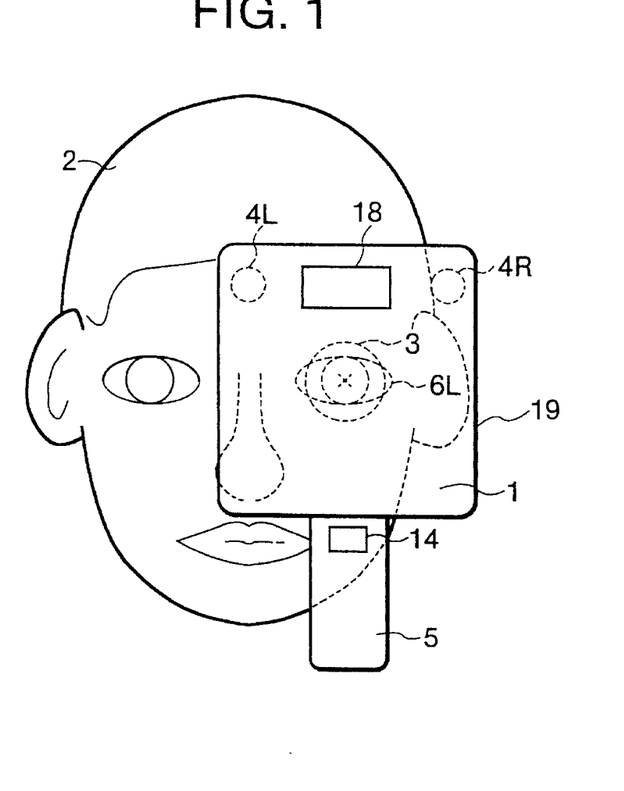
FIG. 1 is an illustration showing a state in which measurement is being effected in the upward direction relative to an eye to be examined by an eye refractive power measuring apparatus according to an embodiment of the present invention.
Figure 2:
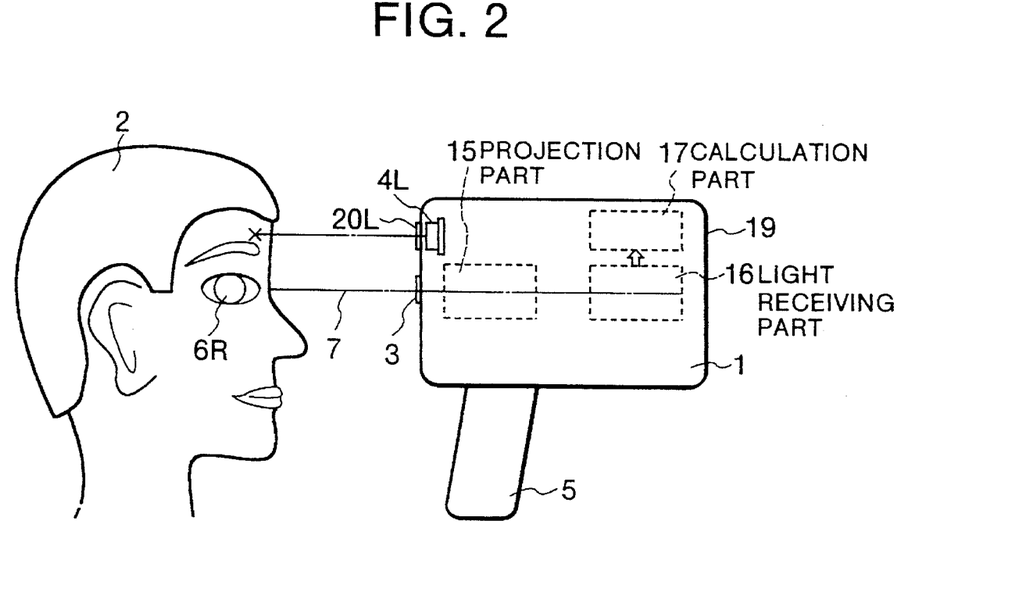
FIG. 2 is an illustration of the eye refractive power measuring apparatus of FIG. 1 as it is seen from a side view.
Figure 3:
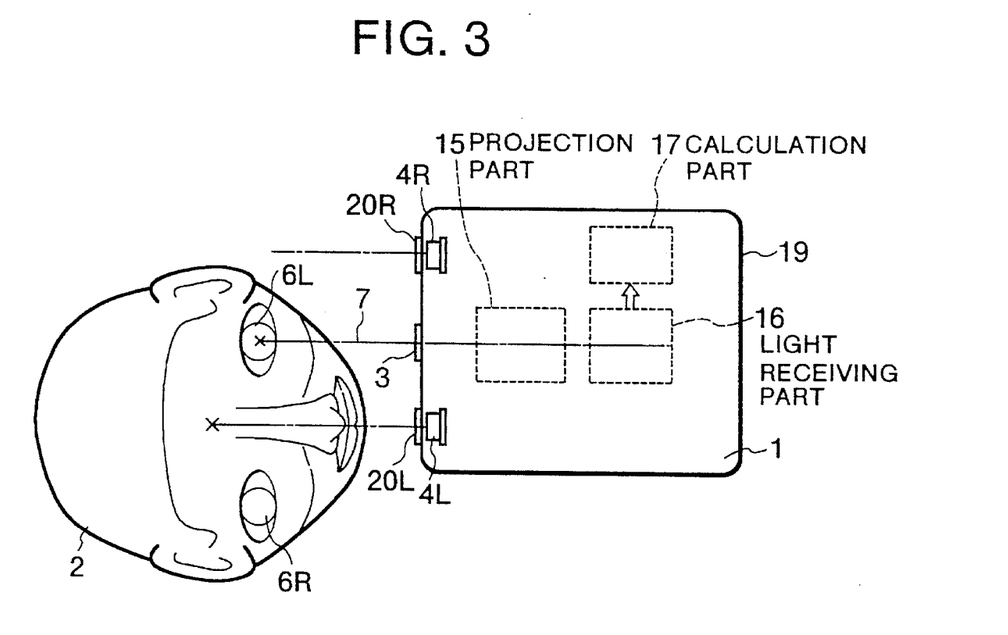
FIG. 3 is an illustration of the eye refractive power measuring apparatus of FIG. 1 as it is seen from above.

FIGS. 1, 2 and 3 show an embodiment of the eye refractive power measuring apparatus of the present invention. The eye refractive power measuring apparatus of this embodiment is a manually holdable type eye refractive power measuring apparatus provided with a grip 5. In these figures, the left eye 6L of an examinee 2 and the measuring optical axis of the eye refractive power measuring apparatus are coincident with each other. Thus, at this time, the measuring apparatus is opposed to an eye to be examined in a proper position.

The eye refractive power measuring apparatus 19 is provided with an apparatus body 1 for effecting measurement, and a grip 5 for use when a measurer (examiner) holds the measuring apparatus in his hand.

Within the apparatus body 1, there are provided a projection part 15 for projecting irradiating light to the fundus of the eye or the cornea of the examinee 2, a light receiving part 16 having a light receiving element for receiving the reflected light of the irradiating light from the fundus of the eye or the cornea, a calculation part 17 for calculating eye refractive power, and the detection part of eye to be examined detecting means for detecting whether the measuring apparatus is opposed to an eye to be examined in a proper position, for example, infrared ray detection elements 4R and 4L for sensing infrared rays emitted by the examinee's face. The infrared ray detection elements 4R and 4L are provided at places located at the right and left above a measuring window 3 which will be described later, as shown, for example, in FIG. 1.

Outside the apparatus body 1, there are provided an output part outputting the result of the calculation by the calculation part 17, for example, a display part 18 for displaying at least the result of the calculation as a numerical value and a message, windows 20R and 20L for the detection elements through which the infrared rays pass, and a measuring window 3 through which the irradiating light passes.

Figure 7:
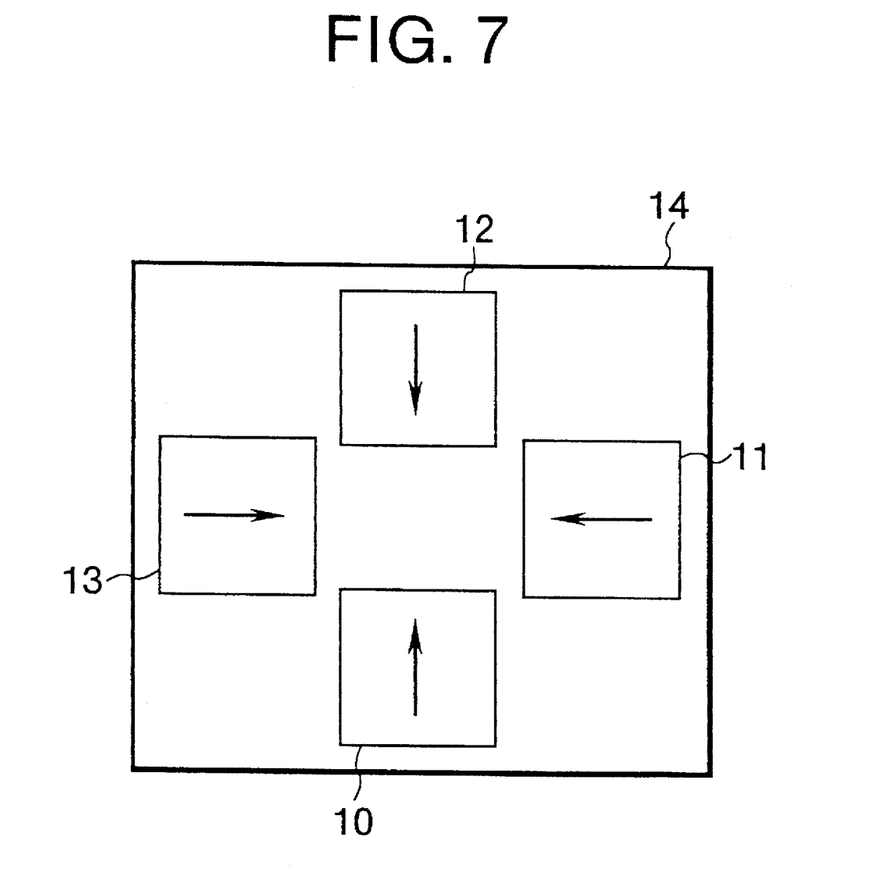
FIG. 7 is an enlarged view showing an input switch.

The grip 5 is provided with direction designating means for inputting information about the direction in which the measuring apparatus is opposed to the eye to be examined and measurement is effected, for example, an input part 14 as shown in FIG. 7. Of course, the input part 14 may be provided on the apparatus body 1 (see FIG. 8). The input part 14 is provided with four ON/OFF switches (upward direction switch 10, downward direction switch 12, leftward direction switch 11 and rightward direction switch 13) for inputting the direction in which the measuring apparatus should be opposed to the eye to be examined as one of the upward direction, the downward direction, the leftward direction and the rightward direction. These four switches are adapted to be exclusively closed.

The calculation part 17 will now be described in detail.

Figure 8:
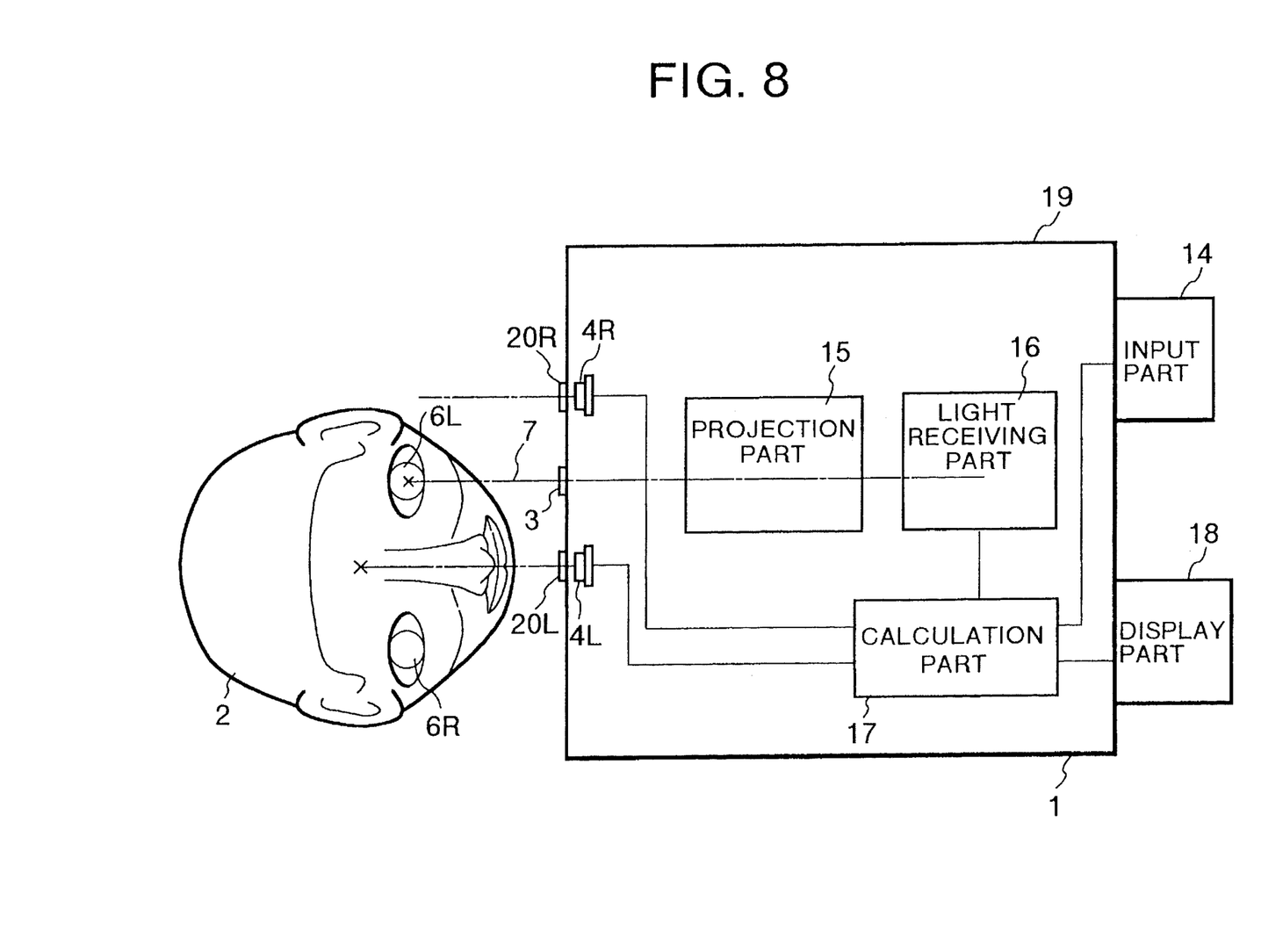
FIG. 8 is a connection diagram of the eye refractive power measuring apparatus of FIG. 1.

As shown in FIG. 8, the calculation part 17 has connected thereto the infrared ray detection elements 4R, 4L, the input part 14, the display part 18 and the light receiving part 16. The infrared ray detection elements 4R and 4L send to the calculation part 17 information about whether the infrared ray detection elements themselves are in their detection states or in their non-detection states (the result of the detection). The input part 14 sends to the calculation part 17 information about whether one of the aforementioned four switches is ON (the result of the input). The calculation part 17 discriminates between the right and left eyes on the basis of said result of the detection and said result of the input. The calculation part 17 may be a computer provided with a CPU, a memory, etc.

The calculation part 17 is provided with combination information as shown in Table 1 below which is used when discriminating between the right and left eyes based on the result of the detection by the infrared ray detection elements 4R and 4L and the result of the input of the input part 14. If the calculation part 17 is provided with memory, this combination information may be stored in the memory. Also, this combination information can be incorporated by hardware logic. Table 1 shows an example of the combination information. Table 1 shows one of the aforementioned four switches of the input part 14 that is ON. Also, the result of the detection by the detection elements 4R and 4L is represented with the non-detection state as "0" and with the detection state as "1".

TABLE 1

| classification of switches being in ON state | substance of detection | | |
|---|---|---|---|
| | detection element 4R | detection element 4L | measured eye |
| upward switch | 1 | 0 | right eye |
| | 0 | 1 | left eye |
| downward switch | 0 | 1 | right eye |
| | 1 | 0 | left eye |
| leftward switch | 0 | 0 | right eye |
| | 1 | 1 | left eye |
| rightward switch | 1 | 1 | right eye |
| | 0 | 0 | left eye |

0: non-detection state
1: detection state

Showing an example of the discrimination between the right and left eyes based on Table 1, when measurement is effected in the direction of the measuring apparatus as shown in FIG. 1, the infrared ray detection element 4R assumes its non-detection state and the infrared ray detection element 4L assumes its detection state. By the detection states of these detection elements and the pre-given information that the measuring apparatus should be opposed to the eye to be examined in the upward direction, i.e., the information that the upward switch 10 is ON, it is discriminated that the eye to be examined is the left eye.

The calculation part 17 also effects the calculation of the direction of an astigmatism axis with the measuring apparatus as the reference, as part of the eye refractive power. It corrects this direction of the astigmatism axis to the direction of the astigmatism axis with the examinee as the reference, on the basis of the information of the direction of the measuring apparatus given from the input part 14.

Description will be made here of the coordinate systems for defining of the direction of the astigmatism axis and information for effecting the correction of the direction of the astigmatism axis.

Figure 9:
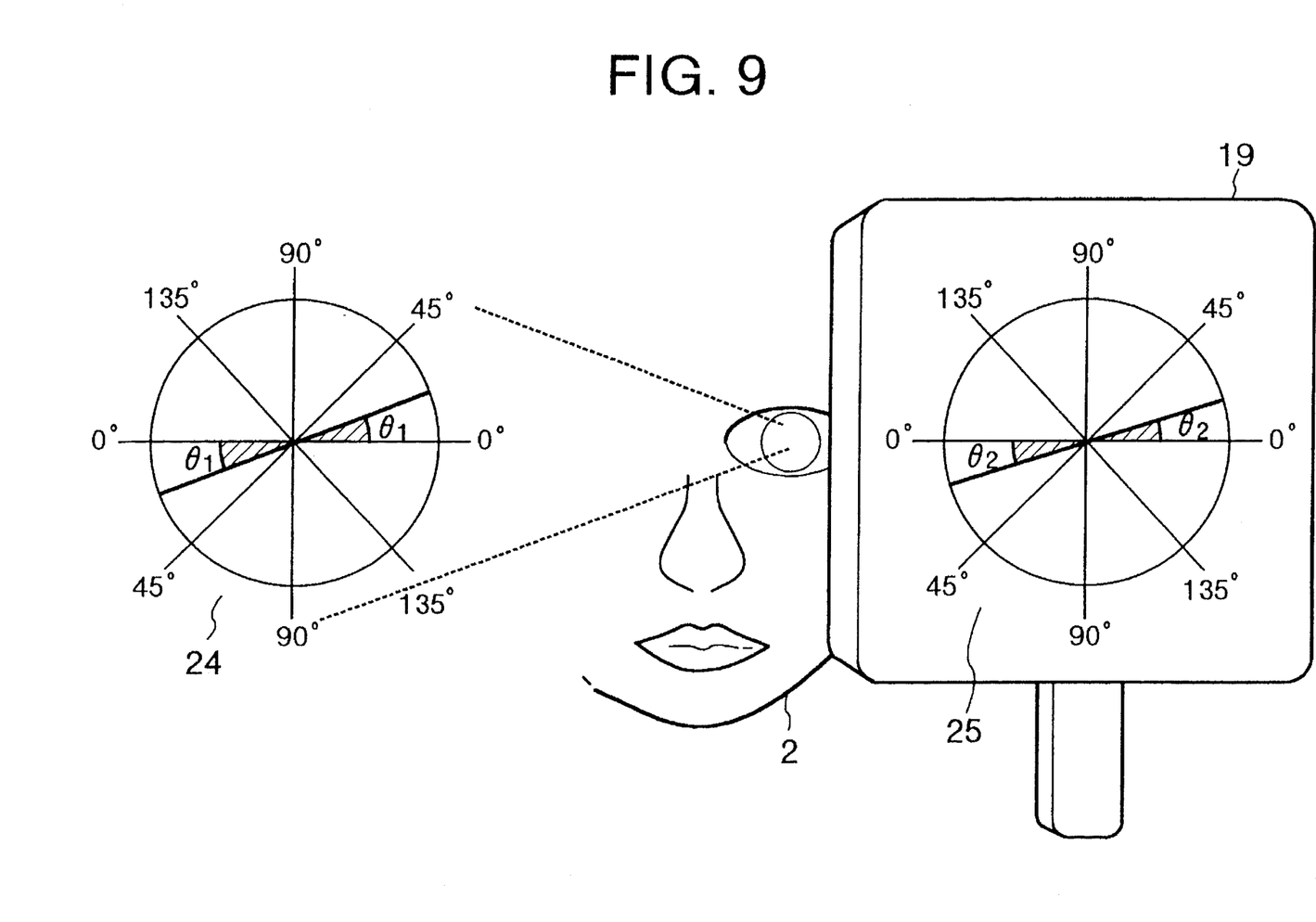
FIG. 9 is an illustration illustrating the direction of an astigmatism axis when the eye refractive power measuring apparatus of FIG. 1 is effecting measurement in an upward direction relative to the eye to be examined.

The coordinate systems for defining of the direction of the astigmatism axis, as shown in FIG. 9, include reference coordinate system 24 for showing the actual direction of the astigmatism axis of the eye to be examined, and coordinate system 25 for measurement on the measuring apparatus 19 used when the direction of the astigmatism axis is measured.

The reference coordinate system 25 is such that as shown, for example, in FIG. 9, the angle formed by a horizontal line passing through substantially the center of the eye to be examined and substantially the center of the other eye is 0°. Also, the angle divisions of the upper side and lower side of the reference coordinate system 24 are symmetrical with the center point of the reference coordinate system 24 as the symmetry point, and are such that angular numbers decrease counter-clockwisely.

The coordinate system 25 for measurement, as shown in FIG. 9, is similar in the manner of giving the angle divisions to the reference coordinate system 24, but is fixed to the measuring apparatus 19.

On the above-described respective coordinate system, the actual and measured directions of the astigmatism axis are represented as $\theta_1$ and $\theta_2$, respectively.

Figure 10:
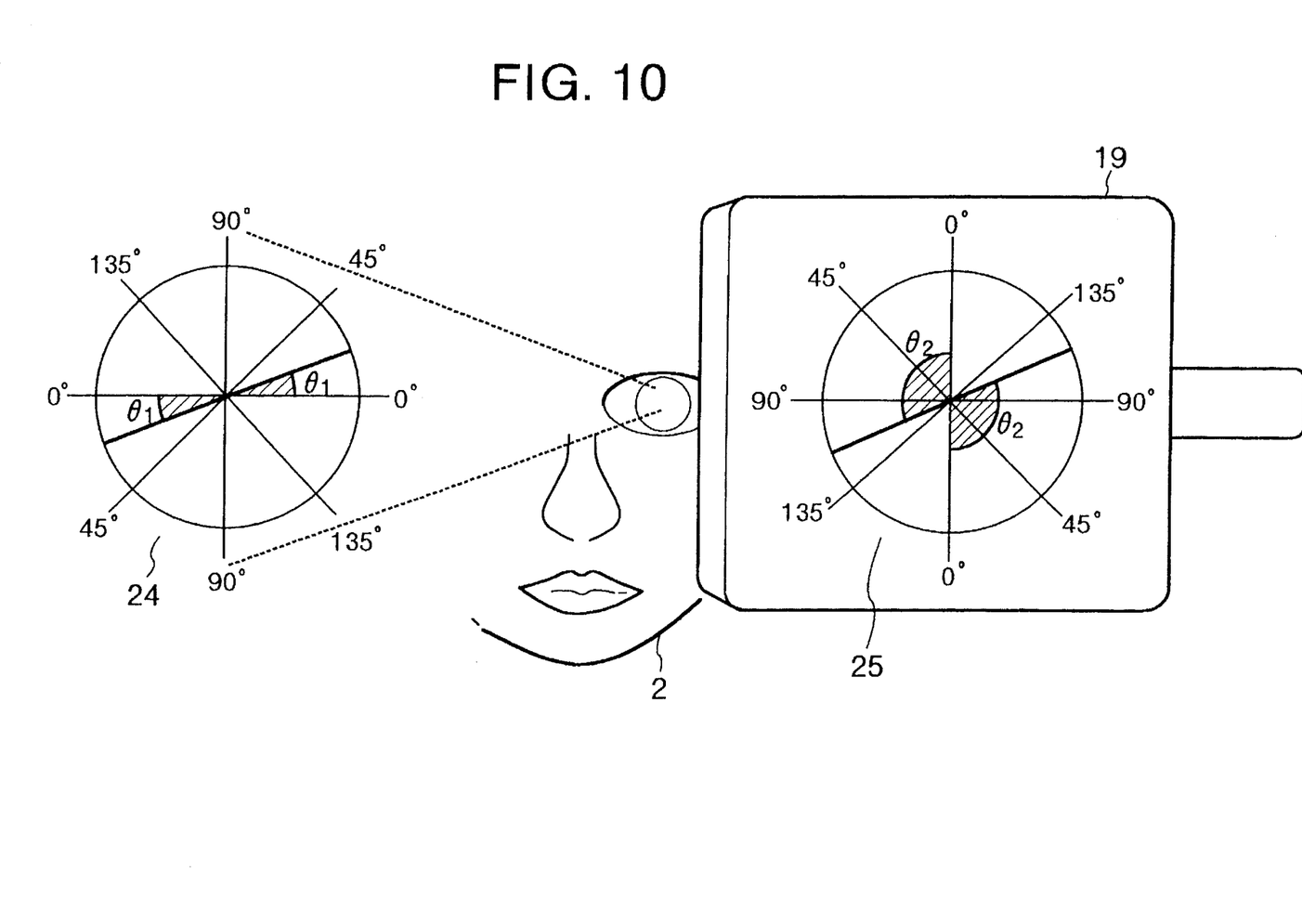
FIG. 10 is an illustration illustrating the direction of an astigmatism axis when the eye refractive power measuring apparatus is effecting measurement in the leftward direction relative to the eye to be examined.
Figure 11:
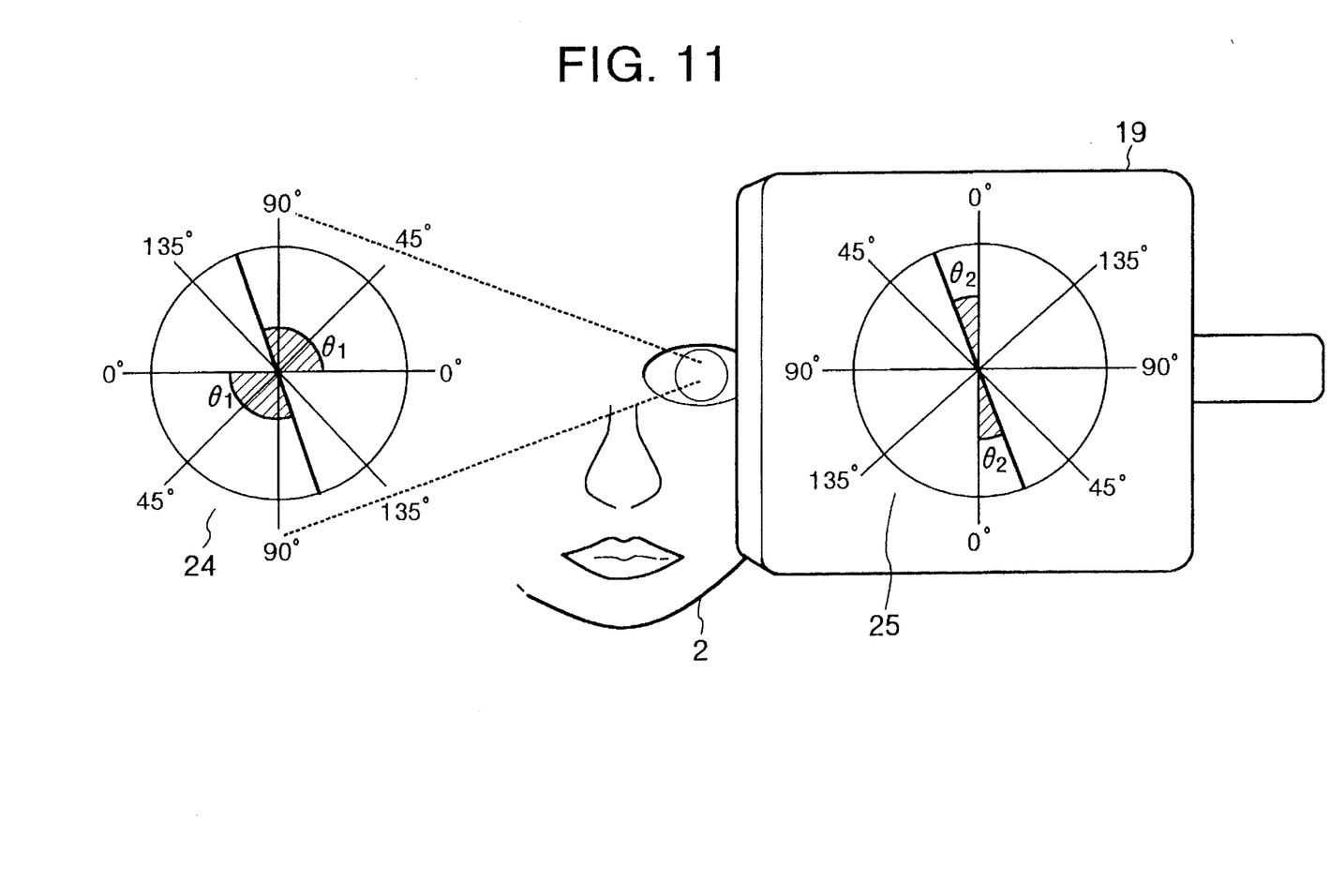
FIG. 11 is an illustration illustrating the direction of an astigmatism axis when the eye refractive power measuring apparatus is effecting measurement in the leftward direction relative to the eye to be examined.
Figure 12:
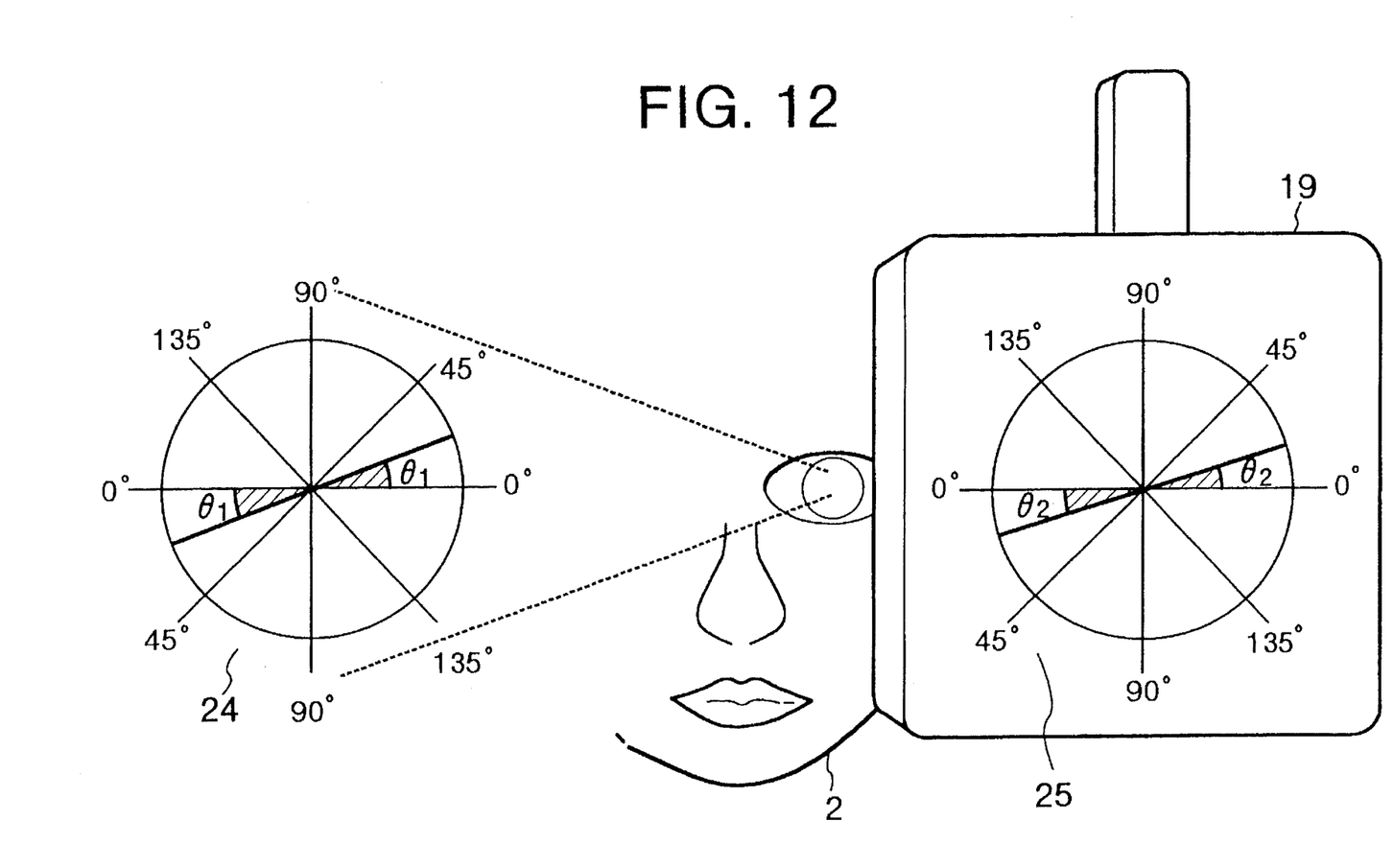
FIG. 12 is an illustration illustrating the direction of an astigmatism axis when the eye refractive power measuring apparatus is effecting measurement in the downward direction relative to the eye to be examined.

As shown in FIGS. 10, 11 and 12, when measurement is effected in a state in which the reference coordinate system 24 and the coordinate system 25 for measurement are not coincident with each other, the actual direction $\theta_1$ of the astigmatism axis and the measured direction $\theta_2$ of the astigmatism axis are deviated from each other. Usually, the direction of the astigmatism axis must be represented on the reference coordinate system 24 and therefore, it is necessary to correct the direction $\theta_2$ of the astigmatism axis. Information for effecting such correction is shown, for example, in Table 2 below. This information can also be provided in the memory of the calculation part 17. The correcting method based on Table 2 will be described later with a method of measuring eye refractive power.

TABLE 2

| classification of switches being in ON state | correction angles relative to the direction of astigmatism | |
|---|---|---|
| | $0° \leq \theta_2 < 90°$ | $90° \leq \theta_2 < 180°$ |
| upward switch | 0° | 0° |
| downward switch | 0° | 0° |
| leftward switch | +90° | −90° |
| rightward switch | +90° | −90° |

In the present embodiment, when the correction angle shown in Table 2 is 0°, the calculation part 17 does not effect the correction of the direction $\theta_2$ of astigmatism axis. This is because the correction angle is 0°, that is, it is not necessary to effect correction.

Description will now be made of a method of measuring eye refractive power by the eye refractive power measuring apparatus 19.

When, as shown in FIGS. 1, 2 and 3, measurement is to be effected with the measuring apparatus opposed to the eye to be examined in the upward direction (the upward direction herein referred to indicates that the measuring apparatus is opposed to the eye to be examined in a normal use state), the upward switch 10 of the input part 14 is first closed. Thereupon, the calculation part 17 recognizes that the measuring apparatus 19 effects measurement in the upward direction. In the state shown in FIGS. 1, 2 and 3, the infrared ray detection element 4L is in a state in which it detects the infrared rays emitted from the forehead of the examinee 2. Also, the infrared ray detection element 4R is at a position off the face of the examinee 2 and is in a state in which it cannot detect the infrared rays emitted from the face of the examinee 2. Accordingly, the result of the detection is that the infrared ray detection element 4R is in its non-detection state and the infrared ray detection element 4L is in its detection state. From this result of the detection and the information that the upward switch 10 is ON, the calculation part 17 discriminates on the basis of the information shown in Table 1 that the eye being measured is the left eye.

If the right eye is being measured, the result of the detection is that the infrared ray detection element 4R is in its detection state and the infrared ray detection element 4L is in its non-detection state. From this result of the detection and the information that the upward switch 10 is ON, the calculation part 17 discriminates on the basis of the information shown in Table 1 that the eye being measured is the right eye.

When the irradiating light is projected onto the eye 6L to be examined of the examinee by the projection part 15, the light receiving part 16 receives the reflected light of the irradiating light from the eye 6L to be examined. When it receives this reflected light, the light receiving part 16 transmits a signal to the calculation part 17. In response to this signal, the calculation part 17 calculates eye refractive power. At this time, from the information that the upward switch 10 is ON, the calculation part 17 does not effect the correction of the direction of an astigmatism axis by the information shown in Table 2. It is because as shown in FIG. 9, the reference coordinate system 24 and the coordinate system 25 for measurement are coincident with each other that it is not necessary to effect the correction. When these coordinate system coincide with each other, the direction $\theta_1$ of the astigmatism axis on the reference coordinate system 24 and the direction $\theta_2$ of the astigmatism axis on the coordinate system 25 for measurement also coincide with each other.

The result of this discrimination between the right and left eyes and the eye refractive power including the directions of the astigmatism axis are displayed by the display part 18.

In FIGS. 1, 2 and 3, the measuring apparatus 19 is upwardly opposed to the eye to be examined, but there is also a case where the measuring apparatus 19 measures while being horizontally opposed to the eye to be examined. Particularly, in the case of a manually holdable measuring apparatus, an examinee lying down on a bed can be measured, and in the case of diagnosis and treatment, measurement is often effected from the bedside in a hospital.

Figure 4:
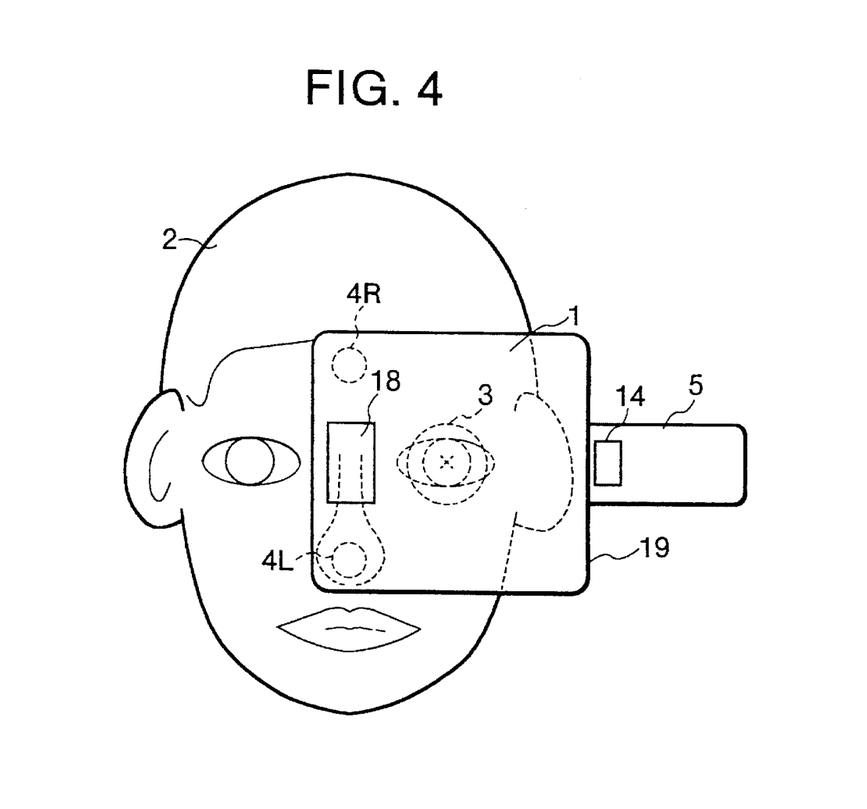
FIG. 4 is an illustration showing a state in which the eye refractive power measuring apparatus of FIG. 1 is effecting left eye measurement in the leftward direction relative to the eye to be examined.

FIG. 4 shows a case where holding the grip 5 of the apparatus body 1, the examiner measures with the apparatus opposed to the eye to be examined in the leftward direction (the leftward direction herein referred to indicates that, relative to the eye to be examined, the measuring apparatus 19 has had its grip counter-clockwise rotated by 90° about the optical axis 7 of the measuring apparatus 19 from the normal use state). In FIG. 4, the principle of the measurement of eye refractive power is similar to that previously described, but in this case, the leftward switch 11 of the input part 14 is first closed. When the examinee's left eye is to be measured as shown in FIG. 4, both of the infrared ray detection elements 4R and 4L assume their detection states. From the result of the detection by these detection elements and the information that the leftward switch 11 is ON, the calculation part 17 discriminates on the basis of the information shown in Table 1 that the eye being measured is the left eye.

The measuring apparatus 19 is measuring in the leftward direction relative to the eye to be examined and therefore, as shown in FIGS. 10 and 11, the direction of the astigmatism axis on the coordinate system 25 for measurement becomes greater by 90° or smaller by 90° than the actual direction of astigmatism axis of the eye to be examined on the reference coordinate system 24. Accordingly, the calculation part 17 corrects the direction of the astigmatism axis by −90° or +90° in accordance with Table 2 based on the information that the leftward switch 11 is ON.

More particularly, when, as shown in FIG. 10, the calculated direction $\theta_2$ of the astigmatism axis on the coordinate system 25 for measurement is 90° or greater and less than 180°, this direction $\theta_2$ of the astigmatism axis is corrected by −90° so as to be capable of representing the direction $\theta_1$ of the astigmatism axis on the reference coordinate system 24. On the other hand, when as shown in FIG. 11, the direction $\theta_2$ of the astigmatism axis on the coordinate system 25 for measurement is 0° or greater and less than 90°, the direction $\theta_2$ of the astigmatism axis is corrected by +90° so as to be capable of representing the direction $\theta_1$ of the astigmatism axis on the reference coordinate system 24.

Figure 5:
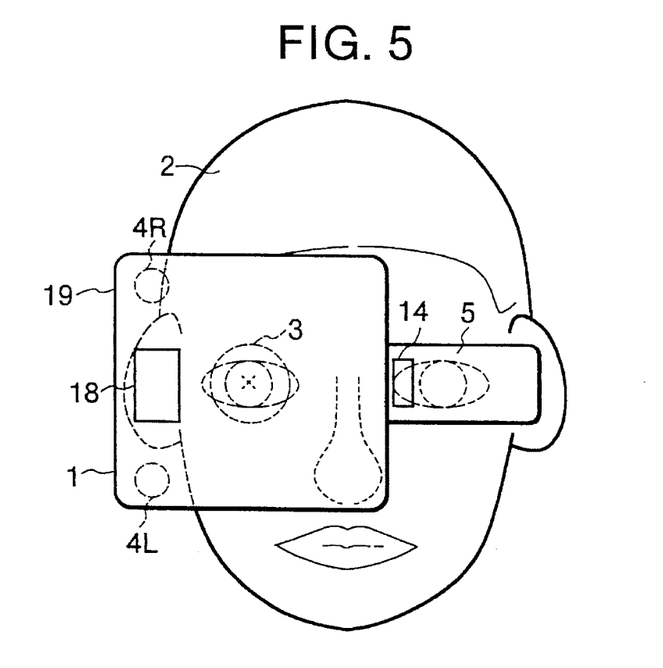
FIG. 5 is an illustration showing a state in which the eye refractive power measuring apparatus of FIG. 1 is effecting right eye measurement in the leftward direction relative to the eye to be examined.

FIG. 5 shows a case where the right eye is measured with the measuring apparatus 19 in the leftward direction.

In this case, both of the infrared ray detection elements 4R and 4L are off the face and assume their non-detection states.

From the result of the detection by these detection elements and the information that the leftward switch 11 is ON, the calculation part 17 discriminates on the basis of Table 1 that the eye being examined is the right eye. Also, the calculation part 17 effects the correction of the direction of the astigmatism axis in accordance with Table 2 based on the information that the leftward switch 11 is ON.

Conversely, when measurement is to be effected with the measuring apparatus is opposed to the eye to be examined in the rightward direction (the rightward direction herein referred to indicates that, relative to the eye to be examined, the measuring apparatus 19 has had its grip 5 counter-clockwisely rotated by 270° about the optical axis 7 of the measuring apparatus 19 from the normal use state), the rightward switch 13 of the input part 14 is first closed. On the basis of Table 1, the calculation 17 discriminates based on the information that the rightward switch 13 is ON and the result of the detection that both of the infrared ray detection elements 4R and 4L are in their detection states, that the eye being examined is the right eye, and discriminates from the result of the detection that both of the infrared ray detection elements 4R and 4L are in their non-detection states, that the eye being examined is the left eye. With regard also to the direction of the astigmatism axis, it corrects on the basis of Table 2.

Figure 6:
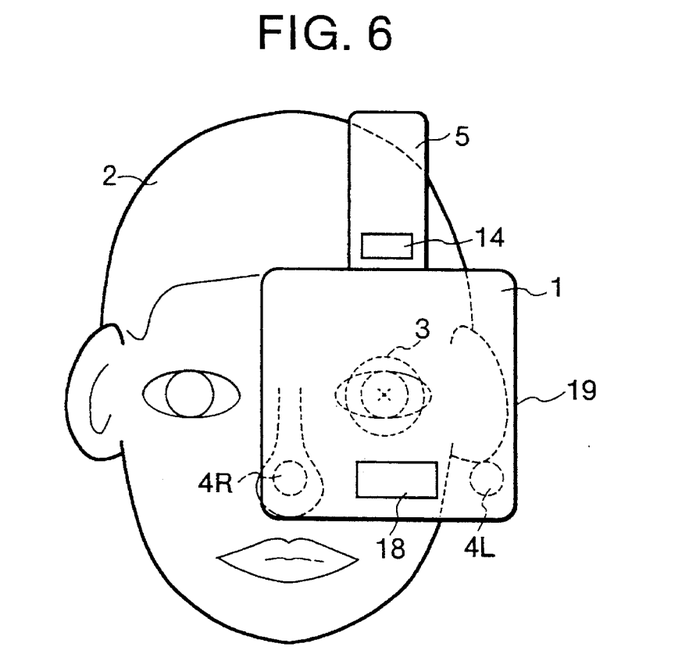

FIG. 6 shows a case where measurement is effected with the measuring apparatus opposed to the eye to be examined in the downward direction (the downward direction herein referred to indicates that relative to the eye to be examined, the measuring apparatus 19 has had its grip 5 counter-clockwisely rotated by 180° about the optical axis 7 of the measuring apparatus 19 from the normal use state).

In this case, the downward switch 12 of the input part 14 is closed in advance. When as shown in FIG. 6, the infrared ray detection element 4R is in its detection state and the infrared ray detection element 4L is in its non-detection state, the calculation part 17 discriminates on the basis of Table 1 that the eye being examined is the left eye. Likewise, when the infrared ray detection element 4L is in its detection state and the infrared ray detection element 4R is in its non-detection state, the calculation part 17 discriminates that the eye being examined is the right eye. At this time, the calculation part 17 does not effect the correction of the direction $\theta_2$ of the astigmatism axis on the basis of Table 2. This is because as shown in FIG. 12, the reference coordinate system 24 and the coordinate system 25 for measurement are coincident with each other.

Figure 15:
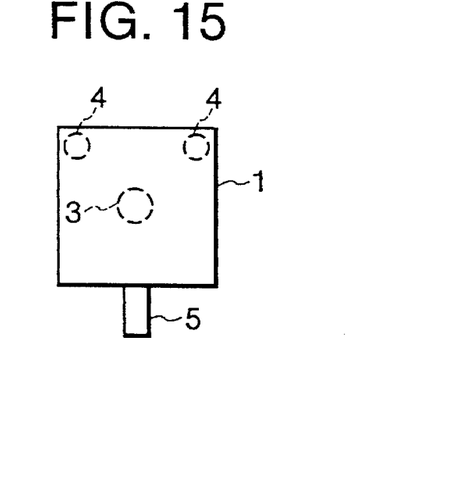
FIG. 15 shows detection elements disposed at two right and left locations in the upper portion.
Figure 16:
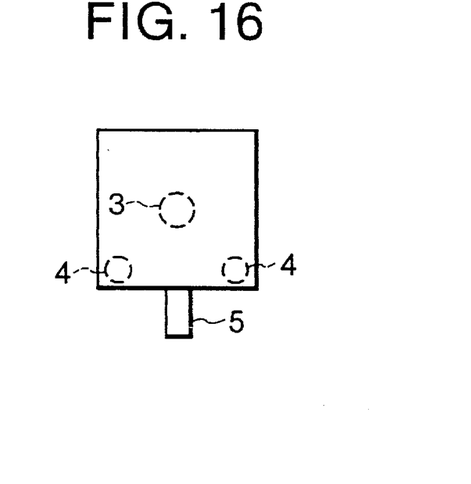
FIG. 16 shows detection elements disposed at two right and left locations in the lower portion.
Figure 17:
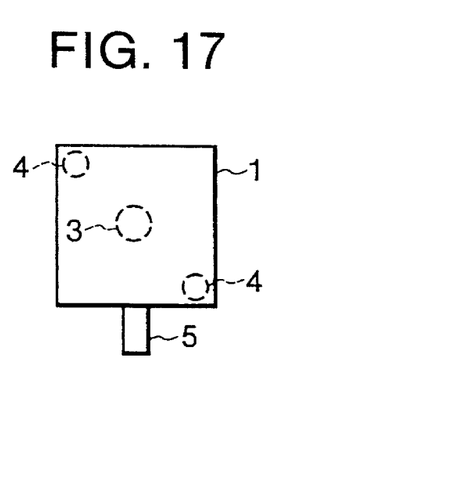
FIG. 17 shows detection elements disposed at the left in the upper portion and the right in the lower portion.
Figure 18:
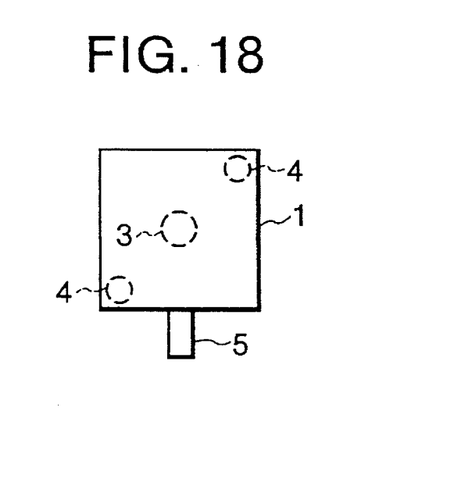
FIG. 18 shows detection elements disposed at the right in the upper portion and the left in the lower portion.
Figure 19:
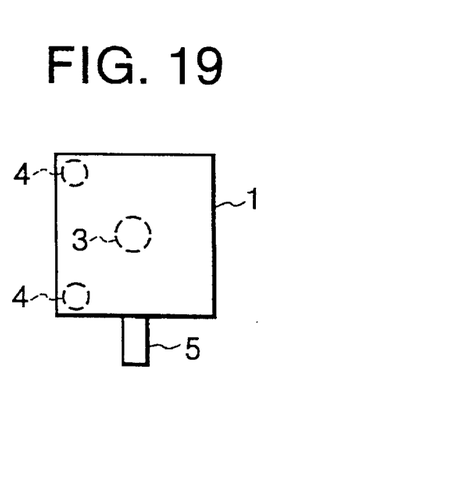
FIG. 19 shows detection elements disposed at the left in the upper portion and the left in the lower portion.
Figure 20:
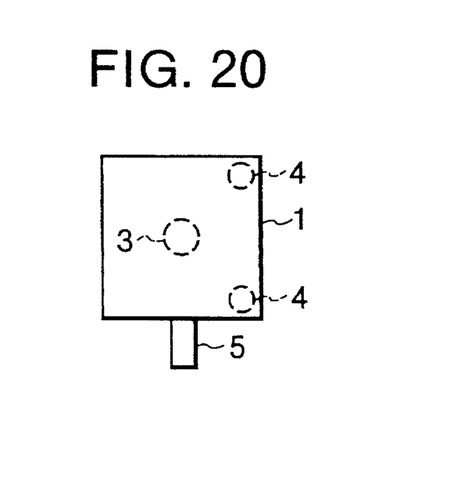
FIG. 20 shows detection elements disposed at the right in the upper portion and the right in the lower portion.

While in the present embodiment, the infrared ray detection elements 4 are disposed at two right and left locations above the measuring window 3 (see FIG. 15), they may be disposed as shown in FIGS. 16 to 20. That is, in FIG. 16, the infrared ray detection elements 4 are disposed at two right and left locations below the measuring window 3. In FIG. 17, the infrared ray detection elements 4 are disposed at the left in the upper portion and the right in the lower portion with the measuring window 3 interposed therebetween. In FIG. 18, the infrared ray detection elements 4 are disposed at the right in the upper portion and the left in the lower portion with the measuring window 3 interposed therebetween. In FIG. 19, the infrared ray detection elements 4 are disposed at the left above the measuring window 3 and the left below the measuring window 3. In FIG. 20, the infrared ray detection elements 4 are disposed at the right above the measuring window 3 and the right below the measuring window 3.

At this time, the calculation part 17 should be provided with the information of the aforedescribed combination table taking the disposed states of the respective detection elements 4 and then the result of the detection by the detection elements 4 into account. From said result of the detection and the result of the input of the input part 14, the calculation part 17 discriminates whether the eye being examined is the right eye or the left eye. In the present embodiment, the number of the infrared ray detection elements 4 is two, but alternatively may be more than two.

Figure 13:
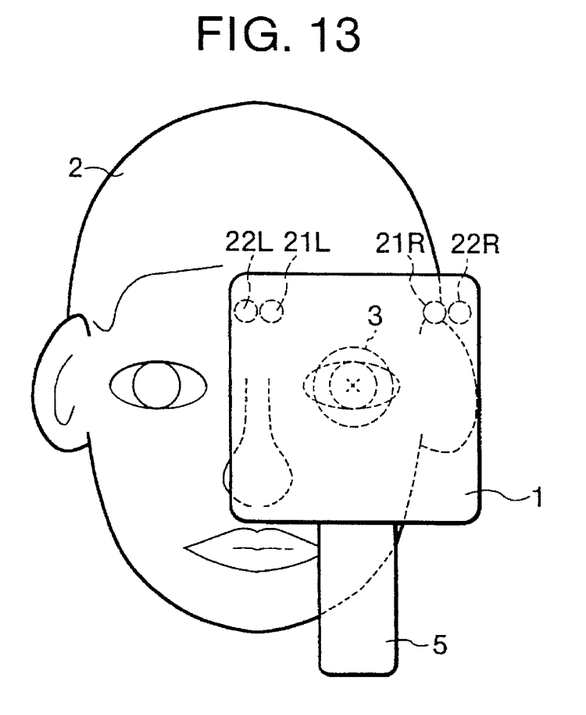
FIG. 13 is an illustration of an eye refractive power measuring apparatus according to an embodiment of the present invention using ultrasonic waves.
Figure 14:
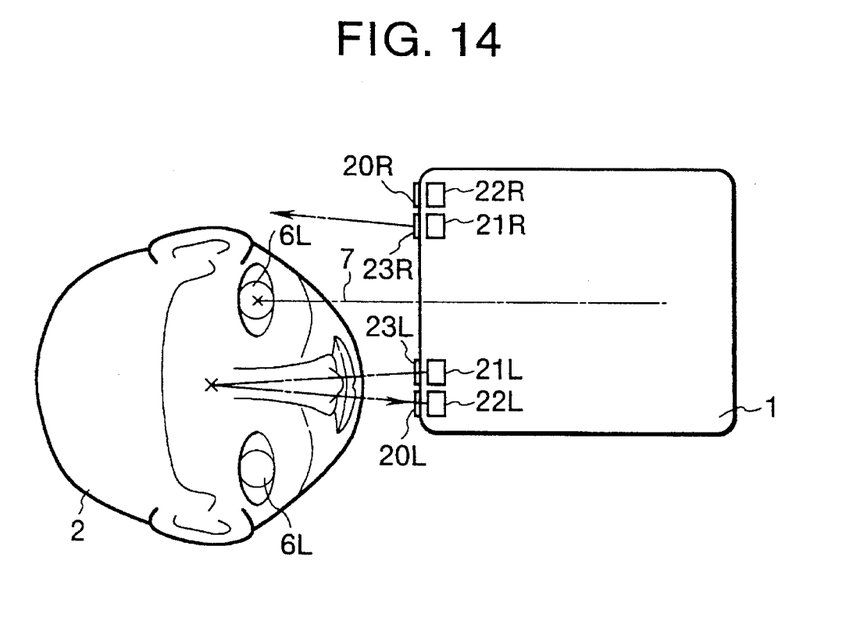
FIG. 14 is an illustration of the eye refractive power measuring apparatus of FIG. 13 as it is seen from above.

Also, as the eye-to-be-examined detecting means, use may be made of ultrasonic waves, besides the method of detecting infrared rays emitted from the examinee's body. An embodiment using ultrasonic waves is shown in FIGS. 13 and 14. In FIGS. 13 and 14, the reference characters 21R and 21L designate ultrasonic wave transmitting elements, and the reference characters 22R and 22L denote ultrasonic wave receiving elements. The discrimination between the presence and absence of a face is effected by ultrasonic waves being transmitted from the ultrasonic wave transmitting elements 21R and 21L through windows 23R and 23L for the ultrasonic wave transmitting elements, and the ultrasonic waves reflected by the examinee's face being detected by the ultrasonic wave receiving elements 22R and 22L.

As the eye-to-be-examined detecting means, it is not preferable to provide a light source in the measuring apparatus, cause irradiating light emitted from the light source to be reflected by the examinee, and effect the discrimination of the examinee's face on the basis of the reflected light. This is because the reflected light is affected by the light of fluorescent lamps or by sunlight. Also, when infrared light is used as the irradiating light with the contraction of the pupil of the eye to be examined taken into account, infrared light is also used for the measurement of eye refractive power and therefore, this infrared light for measurement will be affected. The present embodiment is free of such a problem because it adopts a method of detecting infrared rays emitted from the examinee's body and a method of using ultrasonic waves.

What is claimed is:

1. An eye refractive power measuring apparatus comprising:
   a measuring device for measuring refractive power of eyes to be examined;
   a detecting device having an output state that is dependent upon a direction in which said measuring device is oriented relative to said eyes to be examined and upon which of said eyes to be examined is opposed to said measuring device;
   a direction designating device for designating the direction in which said measuring device is oriented relative to said eyes to be examined, said direction designating device generating a direction designating signal corresponding to the designated direction; and
   a judging device for judging whether the eye opposed to said measuring device is a right eye or a left eye based on the output state of said detecting device and said direction designating signal generated by said direction designating device.

2. An eye refractive power measuring apparatus according to claim 1, wherein said measuring device measures said opposed eye to determine a direction of a cylindrical axis of said opposed eye, and said judging device corrects the measured direction of the cylindrical axis based on said direction designating signal.

3. An eye refractive power measuring apparatus according to claim 1, including a holding portion for manual holding of said measuring device.

4. An eye refractive power measuring apparatus according to claim 1, wherein said direction designating device includes a switch device for designating the direction in which said measuring device is oriented relative to said eyes to be examined.

5. An eye refractive power measuring apparatus according to claim 4, wherein said direction switch device has switches for designating an upward direction, a downward direction, a leftward direction and a rightward direction relative to said eyes to be examined.

6. An eye refractive power measuring apparatus according to claim 1, wherein said detecting device includes a first detecting portion that detects whether said first detecting portion is opposed to a face and a second detecting portion that detects whether said second detecting portion is opposed to said face, and the output state of said detecting device is dependent on detections by said first and second detecting portions.

7. An eye refractive power measuring apparatus according to claim 6, wherein each of said first detecting portion and said second detecting portion has an infrared ray detection element for detecting infrared rays emitted from a portion of said face.

8. An eye refractive power measuring apparatus according to claim 6, wherein each of said first detecting portion and said second detecting portion has a transmitting portion for transmitting an ultrasonic wave toward a portion of said face and a receiving portion for receiving said ultrasonic wave from said portion of said face.

9. An eye refractive power measuring apparatus according to claim 6, wherein, when said measuring device is opposed to one of said eyes to be examined in a predetermined direction of orientation, said first detecting portion is opposed to said face and said second detecting portion is not opposed to said face, and, when said measuring device is opposed to the other of said eyes to be examined in said predetermined direction of orientation, said second detecting portion is opposed to said face and said first detecting portion is not opposed said face.

10. An eye refractive power measuring apparatus according to claim 6, wherein, when said measuring device is opposed to one of said eyes to be examined in a predetermined direction of orientation, both said first detecting portion and said second detecting portion are opposed to said face, and, when said measuring device is opposed to the other of said eyes to be examined in said predetermined direction of orientation, both said first detecting portion and said second detecting portion are not opposed to said face.

11. An eye refractive power measuring apparatus comprising:
   a measuring device for measuring refractive power of eyes to be examined;
   an eye-to-be-examined detecting device that obtains a detection result which is dependent upon a direction in which said measuring device is oriented relative to said eyes to be examined and upon whether said measuring device is opposed to one or the other of said eyes to be examined;
   a switch device for designating the direction in which said measuring device is oriented relative to said eyes to be examined; and
   a judging device for judging whether the eye opposed to said measuring device is a right eye or a left eye based on said detection result of said eye-to-be-examined detecting device and the direction designated by said switch device.

* * * * *